(12) United States Patent
Ji et al.

(10) Patent No.: US 10,611,830 B2
(45) Date of Patent: Apr. 7, 2020

(54) HUMAN ANTIBODY AGAINST ED-B DOMAIN OF FIBRONECTIN AND USES THEREOF

(71) Applicant: HEFEI LIFEON PHARMACEUTICAL CO. LTD., Hefei, Anhui (CN)

(72) Inventors: Junqiu Ji, Anhui (CN); Mei Zhang, Anhui (CN); Meihua Gao, Anhui (CN); Jun Chen, Anhui (CN)

(73) Assignee: HEFEI LIFEON PHARMACEUTICAL CO. LTD., Hefei, Anhui (CN)

( * ) Notice: Subject to any disclaimer, the term of this patent is extended or adjusted under 35 U.S.C. 154(b) by 643 days.

(21) Appl. No.: 14/895,678

(22) PCT Filed: May 28, 2014

(86) PCT No.: PCT/CN2014/078600
§ 371 (c)(1),
(2) Date: Mar. 6, 2016

(87) PCT Pub. No.: WO2014/194784
PCT Pub. Date: Dec. 11, 2014

(65) Prior Publication Data
US 2019/0185550 A1 Jun. 20, 2019

(30) Foreign Application Priority Data
Jun. 6, 2013 (CN) .......................... 2013 1 0221256

(51) Int. Cl.
| | |
|---|---|
| C07K 16/18 | (2006.01) |
| C07K 14/715 | (2006.01) |
| A61K 39/00 | (2006.01) |
| A61P 35/00 | (2006.01) |
| G01N 33/574 | (2006.01) |
| G01N 33/68 | (2006.01) |

(52) U.S. Cl.
CPC .............. *C07K 16/18* (2013.01); *A61P 35/00* (2018.01); *C07K 14/7155* (2013.01); *G01N 33/57415* (2013.01); *G01N 33/57446* (2013.01); *G01N 33/6887* (2013.01); *A61K 2039/505* (2013.01); *C07K 2317/622* (2013.01); *C07K 2317/92* (2013.01); *C07K 2317/94* (2013.01); *C07K 2319/00* (2013.01); *G01N 2333/78* (2013.01)

(58) Field of Classification Search
None
See application file for complete search history.

(56) References Cited

U.S. PATENT DOCUMENTS

| | | | | |
|---|---|---|---|---|
| 2004/0013640 A1* | 1/2004 | Zardi | ................. | A61K 47/6851 424/85.1 |
| 2009/0214423 A1* | 8/2009 | Borsi | ................. | A61K 51/1045 424/1.49 |

OTHER PUBLICATIONS

Pini et al. Design and Use of a Phage Display Library: Human Antibodies With Subnanomolar Affinity Against a Marker of Angiogenesis Eluted From a Two-Dimensional Gel. The Journal of Biological Chemistry. vol. 273, No. 34, Issue of Aug. 21, pp. 21769-21776, 1998 (Year: 1998).*

* cited by examiner

*Primary Examiner* — Maher M Haddad (57) ABSTRACT

The present invention provides an antibody or antibody fragment for specifically recognizing and binding to an ED-B domain of fibronectin. The antibody or antibody fragment can be widely used for in vitro detection and in vivo location of the ED-B protein domain, as well as targeted therapy of tumors.

11 Claims, 4 Drawing Sheets
Specification includes a Sequence Listing.

*Heavy-chain variable region*

```
         10         20         30                    CDR 1 (SEQ ID NO: 8)        40
EVQLLESGGGLVQPGGSLRLSCAASGFTFS    SYAMS    WVRQAPGKGLEWVS
         70         80         90                    CDR 3 (SEQ ID NO: 10)      110
RFTISRDNSKNTLYLQMNSLRAEDTAVYYCAR    HTAPLFDY    WGQGTLVTVSS
```

CDR 2 (SEQ ID NO: 9) RISPSGSSTYYADSVKG

*Linker*

```
         10
GGGGSGGGGSGGGGSS
```

*Light-chain variable region*

```
         10         20                CDR 1 (SEQ ID NO: 11)        30                        40
EIVLTQSPGTLSLSPGERATLSC    RASQSVSSSYLA    WYQQKPGQAPRLLIY
         60         70         80                    CDR 3 (SEQ ID NO: 13)      100
GIPDRFSGSGSGTDFTLTISRLEPEDFAVYYC    QQGRHTP    PTFGQGTKVEIK
```

CDR 2 (SEQ ID NO: 12) KASNLAT

Fig. 5

SEQUENCE LISTING

<160> NUMBER OF SEQ ID NOS: 16

<210> SEQ ID NO 1
<211> LENGTH: 117
<212> TYPE: PRT
<213> ORGANISM: Artificial Sequence
<220> FEATURE:

<223> OTHER INFORMATION: Synthesis

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Thr Ala Pro Leu Phe Asp Tyr Trp Gly Gln Gly Thr Leu
            100                 105                 110

Val Thr Val Ser Ser
        115

<210> SEQ ID NO 2
<211> LENGTH: 351
<212> TYPE: DNA
<213> ORGANISM: Artificial Sequence
<220> FEATURE:
<223> OTHER INFORMATION: Sythesis

<400> SEQUENCE: 2
gaagtgcagc tgttggaatc tggggggtggc ttggtacagc ctgggggggtc cctgcgtctc      60 tcctgtgcag ccagcggctt cacctttagt agctatgcca tgagctgggt ccgccaggct     120
ccagggaaag gcctggaatg ggtcagtcgt attagtccga gtggcagcag tacatactac     180
gcagactccg tgaaaggtcg cttcaccatc tcccgtgaca attccaaaaa cacgctgtat     240
ctgcaaatga acagcctgcg tgccgaagac accgccgtat attactgtgc gcgtcatact     300
gcgcctctgt tcgattactg gggccagggc accctggtca ccgtctccag t              351

<210> SEQ ID NO 3
<211> LENGTH: 108
<212> TYPE: PRT
<213> ORGANISM: Artificial Sequence
<220> FEATURE:
<223> OTHER INFORMATION: Synthesis

<400> SEQUENCE: 3

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Lys Ala Ser Asn Leu Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Gly Arg His Thr Pro
                85                  90                  95

Pro Thr Phe Gly Gln Gly Thr Lys Val Glu Ile Lys

<210> SEQ ID NO 4
<211> LENGTH: 324
<212> TYPE: DNA
<213> ORGANISM: Artificial Sequence
<220> FEATURE:
<223> OTHER INFORMATION: Synthesis

<400> SEQUENCE: 4

```
gaaattgtgt tgacgcagtc tccaggcacc ctgtctttgt ctccaggtga aagagccacc      60
ctctcttgcc gtgccagtca gagtgttagc agcagctact tagcctggta ccagcagaaa     120
cctggccagg ctccacgtct gctgatctat aaagcttcta acctggccac cggcatccca     180
gaccgtttca gtggcagtgg ctctggtaca gacttcactc tcaccatcag ccgcctggag     240
cctgaagatt ttgcagtgta ttactgtcag cagggtcgtc atacgccgcc taccttcggc     300
caaggcacca aggtggaaat caaa                                            324
```

<210> SEQ ID NO 5
<211> LENGTH: 16
<212> TYPE: PRT
<213> ORGANISM: Artificial Sequence
<220> FEATURE:
<223> OTHER INFORMATION: Synthesis

<400> SEQUENCE: 5

Gly Gly Gly Gly Ser Gly Gly Gly Gly Ser Gly Gly Gly Gly Ser Ser
1               5                   10                  15

<210> SEQ ID NO 6
<211> LENGTH: 48
<212> TYPE: DNA
<213> ORGANISM: Artificial Sequence
<220> FEATURE:
<223> OTHER INFORMATION: Synthesis

<400> SEQUENCE: 6

```
ggtggtggcg gttcaggcgg tggtggctct ggtggcggtg ggagctct                   48
```

<210> SEQ ID NO 7
<211> LENGTH: 17
<212> TYPE: PRT
<213> ORGANISM: Artificial Sequence
<220> FEATURE:
<223> OTHER INFORMATION: Synthesis

<400> SEQUENCE: 7

Ala Ala Ala Ser Ser Ser Gly Ser Ser Ser Ser Gly Ser Ser Ser Ser
1               5                   10                  15

Gly

<210> SEQ ID NO 8
<211> LENGTH: 5
<212> TYPE: PRT
<213> ORGANISM: Artificial Sequence
<220> FEATURE:
<223> OTHER INFORMATION: Synthesis

<400> SEQUENCE: 8

Ser Tyr Ala Met Ser
1               5

<210> SEQ ID NO 9

```
<211> LENGTH: 17
<212> TYPE: PRT
<213> ORGANISM: Artificial Sequence
<220> FEATURE:
<223> OTHER INFORMATION: Synthesis

<400> SEQUENCE: 9

Arg Ile Ser Pro Ser Gly Ser Ser Thr Tyr Tyr Ala Asp Ser Val Lys
1               5                   10                  15
Gly

<210> SEQ ID NO 10
<211> LENGTH: 8
<212> TYPE: PRT
<213> ORGANISM: Artificial Sequence
<220> FEATURE:
<223> OTHER INFORMATION: Synthesis

<400> SEQUENCE: 10

His Thr Ala Pro Leu Phe Asp Tyr
1               5

<210> SEQ ID NO 11
<211> LENGTH: 12
<212> TYPE: PRT
<213> ORGANISM: Artificial Sequence
<220> FEATURE:
<223> OTHER INFORMATION: Synthesis

<400> SEQUENCE: 11

Arg Ala Ser Gln Ser Val Ser Ser Tyr Leu Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Synthesis

<400> SEQUENCE: 12

Lys Ala Ser Asn Leu Ala Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Synthesis

<400> SEQUENCE: 13

Gln Gln Gly Arg His Thr Pro
1               5

<210> SEQ ID NO 14
<211> LENGTH: 8
<212> TYPE: PRT
<213> ORGANISM: Artificial Sequence
<220> FEATURE:
<223> OTHER INFORMATION: Synthesis

<400> SEQUENCE: 14

Ala Ala Ala Ala Ala Ala Ala Ala
1               5
```

<210> SEQ ID NO 15
<211> LENGTH: 241
<212> TYPE: PRT
<213> ORGANISM: Artificial Sequence
<220> FEATURE:
<223> OTHER INFORMATION: Synthesis

<400> SEQUENCE: 15

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Thr Ala Pro Leu Phe Asp Tyr Trp Gly Gln Gly Thr Leu
            100                 105                 110

Val Thr Val Ser Ser Gly Gly Gly Gly Ser Gly Gly Gly Gly Ser Gly
        115                 120                 125

Gly Gly Gly Ser Ser Glu Ile Val Leu Thr Gln Ser Pro Gly Thr Leu
    130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Lys Ala Ser Asn Leu Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Gly Arg His Thr Pro Pro Thr Phe Gly Gln Gly Thr Lys Val Glu Ile
225                 230                 235                 240

Lys
```

<210> SEQ ID NO 16
<211> LENGTH: 392
<212> TYPE: PRT
<213> ORGANISM: Artificial Sequence
<220> FEATURE:
<223> OTHER INFORMATION: Synthesis

<400> SEQUENCE: 16

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Arg Ile Ser Pro Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
```

-continued

```
            65                  70                  75                  80
Leu Gln Met Asn Ser Leu Arg Ala Glu Asp Thr Ala Val Tyr Tyr Cys
                85                  90                  95

Ala Arg His Thr Ala Pro Leu Phe Asp Tyr Trp Gly Gln Gly Thr Leu
                100                 105                 110

Val Thr Val Ser Ser Gly Gly Gly Gly Ser Gly Gly Gly Gly Ser Gly
                115                 120                 125

Gly Gly Gly Ser Ser Glu Ile Val Leu Thr Gln Ser Pro Gly Thr Leu
        130                 135                 140

Ser Leu Ser Pro Gly Glu Arg Ala Thr Leu Ser Cys Arg Ala Ser Gln
145                 150                 155                 160

Ser Val Ser Ser Ser Tyr Leu Ala Trp Tyr Gln Gln Lys Pro Gly Gln
                165                 170                 175

Ala Pro Arg Leu Leu Ile Tyr Lys Ala Ser Asn Leu Ala Thr Gly Ile
                180                 185                 190

Pro Asp Arg Phe Ser Gly Ser Gly Ser Gly Thr Asp Phe Thr Leu Thr
                195                 200                 205

Ile Ser Arg Leu Glu Pro Glu Asp Phe Ala Val Tyr Tyr Cys Gln Gln
        210                 215                 220

Gly Arg His Thr Pro Pro Thr Phe Gly Gln Gly Thr Lys Val Glu Ile
225                 230                 235                 240

Lys Ala Ala Ala Ser Ser Ser Gly Ser Ser Ser Ser Gly Ser Ser Ser
                245                 250                 255

Ser Gly Ala Pro Thr Ser Ser Ser Thr Lys Lys Thr Gln Leu Gln Leu
                260                 265                 270

Glu His Leu Leu Leu Asp Leu Gln Met Ile Leu Asn Gly Ile Asn Asn
        275                 280                 285

Tyr Lys Asn Pro Lys Leu Thr Arg Met Leu Thr Phe Lys Phe Tyr Met
        290                 295                 300

Pro Lys Lys Ala Thr Glu Leu Lys His Leu Gln Cys Leu Glu Glu Glu
305                 310                 315                 320

Leu Lys Pro Leu Glu Glu Val Leu Asn Leu Ala Gln Ser Lys Asn Phe
                325                 330                 335

His Leu Arg Pro Arg Asp Leu Ile Ser Asn Ile Asn Val Ile Val Leu
                340                 345                 350

Glu Leu Lys Gly Ser Glu Thr Thr Phe Met Cys Glu Tyr Ala Asp Glu
        355                 360                 365

Thr Ala Thr Ile Val Glu Phe Leu Asn Arg Trp Ile Thr Phe Cys Gln
        370                 375                 380

Ser Ile Ile Ser Thr Leu Thr Ala
385                 390
```

HUMAN ANTIBODY AGAINST ED-B DOMAIN OF FIBRONECTIN AND USES THEREOF

CROSS REFERENCE OF RELATED APPLICATION

This is a U.S. National Stage under 35 U.S.C 371 of the International Application PCT/CN2014/078600, filed May 28, 2014, which claims priority under 35 U.S.C. 119(a-d) to CN 201310221256.0, filed Jun. 6, 2013.

BACKGROUND OF THE PRESENT INVENTION

Field of Invention

The present invention relates to a monoclonal antibody technology, a phage display technology and a gene recombination technology, and particularly relates to an antibody or antibody fragment for binding to an ED-B domain of fibronectin (FN). Additionally, the present invention also relates to a method for preparing the monoclonal antibody and a pharmaceutical composition including the monoclonal antibody.

Description of Related Arts

Commonly-used tumor therapy methods include chemotherapy and radiotherapy methods, which affect physiological functions of normal organs and reduce the immune ability and life quality of a patient while killing a cancer cell due to their low specificity and significant toxic or side effect on normal tissues. A method for improving the specificity of a tumor therapeutic drug is targeted killing of a tumor by targeting the drug to a tumor cell via an antibody or antibody fragment which can recognize a tumor cell marker. Achievement of this method firstly requires finding a tumor marker capable of being expressed on an external surface of a cell membrane, i.e., a protein which is only expressed on the surface or in the matrix of a tumor cell, but is expressed with a small amount or even not expressed in a normal cell or tissue.

Fibronectin is a multifunctional glycoprotein existing widely in extracellular matrix, blood plasma and other body fluids, which is expressed by epithelial cells, endothelial cells, fibroblast cells, liver cells, decidual cells, extravillous trophoblast cells and the like. FN participates in adhesion, cytomorphosis and distribution of cells, and formation of blood vessels.

The FN gene is about 75 kb long, includes about 50 exons, and essentially consists of types I, II, and III homologous repeating units. ED-B is included in the type III repetitive sequence of the FN, and is a complete repeat composed of 91 amino acids and coded by a single exon. During expression of the FN gene, two cases exist, one is FN(B+) including an ED-B domain and the other is FN(B−) including no ED-B domain. These two cases are considered as playing an important role in an individual development process. The FN(B+) is expressed with a small amount in a normal tissue of an adult, but is highly expressed during an injury process, a disease process or a wound healing process, and particularly during a tumor growth process, and thus is also referred to as a carcinoembryonic gene. The FN(B+) including the ED-B domain is highly expressed in for example cells of gastric cancer, colorectal cancer, lung cancer, breast cancer and the like. As shown by in vitro immunohistochemical detection and in vivo targeted localization, the FN(B+) is highly expressed in blood vessels in varied types of tumor tissues, but is not expressed in a normal tissue of an adult, and thus is a marker protein of a tumor tissue.

Therefore, a targeted antibody is developed based on the ED-B domain, which can be used for targeting a candidate drug such as cytotoxin and the like to a tumor location so as to achieve a therapeutic aim by effectively inhibiting or killing tumor cells and meanwhile reduce the damage to normal tissues and toxic or side effects.

The screening or drug development of an antibody against the ED-B has a history of more than 20 years. For example a murine-derived monoclonal antibody BC-1 obtained through a hybridoma technique (Carnemolla, Leprini et al. 1992) can specifically recognize the FN (B+) of new human blood vessels and does not cross-react with the FN(B−).

Additionally, a Fab-type murine-derived antibody MOR03255 obtained through mouse immunity and affinity maturation conducted by means of a phage display technology has a maximum affinity up to 30 pM. MOR03255 has the characteristic of neutralizing an antibody, which binds to the ED-B to inhibit the adhesion between human dermal microvascular endothelial (HDMVE) cells and extracellular matrix and thus the formation of new blood vessels, such that the tumor tissues are lack of nutrition due to the absence of blood vessels. Therefore, MOR03255 shows a significant inhibition effect on tumor growth in vivo experiments.

However, as demonstrated by a research, when a murine-derived antibody drug is administrated in the human body, a serious human anti-murine antibody (HAMA) reaction is caused, and other side effects may also be caused, such as an allergic response, a blood disease and damage to kidney. Furthermore, such an antibody has a short half life, which affects the therapeutic effect. Therefore, the murine-derived antibodies BC-1 and MOR03255 have some limitations. Now the murine-derived antibody is gradually replaced by a humanized antibody and a fully humanized antibody.

Since the amino acid sequence of human ED-B is 100% homologous with that of mice's ED-B, the immune system of mice recognizes the human ED-B as its own protein and thus seldomly generates an immune response to the ED-B domain of human. Therefore, the development of the murine-derived antibody against ED-B is often counter-productive. Now with the aid of genetic engineering techniques, an antibody with a specific function is obtained by directly expressing a synthesized antibody gene via the use of the phage display technique and then screening, without using any immune system of a higher animal, and thus a technique for developing recombinant humanized antibodies is available. Currently reported humanized antibodies against ED-B include CGS-1, CGS-2, L19 and the like (Carnemolla, Neri et al. 1996, Pini, Viti et al. 1998), which all have high specificity and respectively have affinities of $5.4 \times 10^{-8}$ M, $1.1 \times 10^{-9}$ M and $8.7 \times 10^{-10}$ M as detected by BIAcore. Particularly the clinical research of the antibody L19 sufficiently demonstrates that a specific antibody drug developed against ED-B has a significant effect of inhibiting or killing tumors.

We have obtained a specific single-chain antibody by screening with the aid of synthesis of antibody genes and the phage display technique. The antibody can directly recognize a single ED-B domain and FN(B+), as well as fusion forms of ED-B with other proteins, e.g., GST-ED-B and the like. The antibody obtained by screening does not need affinity maturation, and thus is superior to other disclosed humanized single-chain antibodies against ED-B. Additionally, the binding between the obtained antibody and an antigen is hardly ever dissociated, as detected by BIAcore. These features demonstrate that the obtained antibody can bind to ED-B, and the very high affinity of the antibody enables the binding between the antibody and an antigen to be hardly ever dissociated, such that the antibody can be targeted to and highly enriched at a tissue site which expresses FN(B+) and is hardly ever dissociated again and diffused into normal tissues.

The obtained antibody can be used for development of anti-tumor drugs, e.g., radioisotopic labeling of the antibody, fusion of the antibody with cytotoxin, coupling of the antibody with chemical drugs and the like. With the aid of the obtained antibody, a drug is highly enriched in tumor tissues which highly express FN(B+), so as to achieve targeted killing of tumor cells and improve the drug efficacy while having small damage to normal tissues. Since fully humanized antibodies are human homologous proteins and have low immunogenicity in the human body, in general the HAMA reaction less likely occurs, so that the fully humanized antibodies have lower toxic or side effects than murine-derived antibodies. The structure form of the single-chain antibody enables miniaturization of antibody drugs and improves the permeability of the antibody into the human body, such that the antibody can get into the tumor tissues through tumor blood vessels; and the single-chain antibody may be flexibly varied into antibodies of various forms, e.g. a natural antibody structure, a minibody, a double-antibody, a fusion form of multiple antibodies and the like. By changing the structure form of the antibody, the stability, permeability, use and the like of the antibody can be varied. Furthermore, the obtained antibody can be developed to serve as a tumor diagnostic reagent for in vivo and in vitro detection of tumor tissues, or used for development of various other types of immune-related reagents.

SUMMARY OF THE PRESENT INVENTION

Through a lot of creative works, the inventor obtains a recombinant monoclonal antibody or antibody fragment against a human ED-B protein domain, wherein said antibody fragment is preferably an antigen-binding fragment; and the antibody or antibody fragment can effectively bind to fibronectin (FN) including an ED-B domain (abbreviated as FN(B+)), and can be used for detection and diagnosis of FN(B+), as well as targeted therapy of tumors which highly express FN(B+).

Therefore, the present invention provides an antibody or antibody fragment for specifically recognizing and binding to an ED-B domain of human fibronectin (FN).

In a specific implementation, the antibody or antibody fragment includes an amino acid sequence of the CDR3 region of a heavy-chain variable region (VH), wherein the CDR3 region includes the amino acid sequence of HTAPLFDY (SEQ ID NO: 10).

In another specific implementation, the antibody or antibody fragment includes an amino acid sequence of the CDR3 region of a light-chain variable region (VL), wherein the CDR3 region includes the amino acid sequence of QQGRHTP (SEQ ID NO: 13).

In another specific implementation, the antibody or antibody fragment includes a VH CDR3 having the amino acid sequence of HTAPLFDY (SEQ ID NO: 10) and a VL CDR3 having the amino acid sequence of HTAPLFDY (SEQ ID NO: 10).

In another specific implementation, the antibody or antibody fragment includes three VH CDRs. The amino acid sequences of the CDRs are respectively SYAMS (SEQ ID NO: 8), RISPSGSSTYYADSVKG (SEQ ID NO: 9) and HTAPLFDY (SEQ ID NO: 10).

In another specific implementation, the antibody or antibody fragment includes three VL CDRs. The amino acid sequences of the CDRs are respectively RASQSVSSSYLA (SEQ ID NO: 11), KASNLAT (SEQ ID NO: 12) and QQGRHTP (SEQ ID NO: 13).

In another specific implementation, the antibody or antibody fragment includes three VH CDRs and three VL CDRs, wherein the amino acid sequences of the three VH CDRs are respectively SYAMS (SEQ ID NO: 8), RISPSGSSTYYADSVKG (SEQ ID NO: 9) and HTAPLFDY (SEQ ID NO: 10); and the amino acid sequences of the three VL CDRs are respectively RASQSVSSSYLA (SEQ ID NO: 11), KASNLAT (SEQ ID NO: 12) and QQGRHTP (SEQ ID NO: 13).

In another specific implementation, the antibody or antibody fragment includes a VH having the amino acid sequence as shown in SEQ ID NO: 1.

In another specific implementation, the antibody or antibody fragment includes a VL having the amino acid sequence as shown in SEQ ID NO: 3.

In another specific implementation, the antibody or antibody fragment includes a VH having the amino acid sequence as shown in SEQ ID NO: 1, and a VL having the amino acid sequence as shown in SEQ ID NO: 3.

In another specific implementation, the antibody or antibody fragment is a monoclonal antibody with an equilibrium binding/dissociation constant (KD) of $1\times10^{-8}$ M or less, $1\times10^{-9}$ M or less, or $1\times10^{-10}$ M or less.

In another specific implementation, the antibody or antibody fragment is a monomer or polymer.

In another specific implementation, the antibody or antibody fragment is a mammal-derived antibody sequence, and particularly a human-derived antibody sequence.

In another specific implementation, the antibody or antibody fragment directly binds to the ED-B protein domain. Particularly, the ED-B protein domain may be an independent recombinant ED-B protein, or a recombinant protein formed through fusion of the ED-B protein with other proteins, or a natural fibronectin including the ED-B domain. More particularly, the ED-B protein domain may be derived from humans, mice, rats, chickens or other species. More particularly, the ED-B protein domain may be a glycosylated protein or a non-glycosylated protein.

In a specific implementation, the antibody fragment may be a monovalent and micromolecular antibody, such as a single-chain antibody, a single-domain antibody, a hyper-variable region polypeptide or the like, and Fab; or a multivalent and micromolecular antibody, such as a double-chain antibody, a three-chain antibody, and a minibody.

In a specific implementation, the antibody is a human immunoglobulin IgG.

On the other hand, the present invention provides a pharmaceutical composition including the aforementioned antibody or antibody fragment.

In an implementation, the pharmaceutical composition further includes but not limited to a fusion protein, a radioactive isotope, a chemical drug, a nanoparticle and the like. In a specific implementation, the pharmaceutical composition is used for diagnosis or therapy of tumor-related diseases.

On the other hand, the present invention provides use of the aforementioned antibody or antibody fragment, or the pharmaceutical composition thereof in prevention, diagnosis and therapy of cancer-related diseases. On the other hand, the present invention provides use of the aforementioned antibody or antibody fragment, or the pharmaceutical composition thereof in preparation of a drug for prevention, diagnosis and therapy of cancer-related diseases. Particularly, the cancer-related disease is cancer in which the FN(B+) including the ED-B domain is expressed. The cancer may be nasopharyngeal cancer, larynx cancer, oesophagus cancer, cardiac cancer, gastric cancer, colorectal cancer, lung cancer, liver cancer, pancreatic cancer, melanoma, fibrosarcoma or breast cancer; and more particularly, the cancer-related disease is gastric cancer, colorectal cancer, lung cancer or breast cancer.

On the other hand, the present invention provides a diagnostic kit including the aforementioned antibody or antibody fragment, which can be used for diagnosis of in vivo distribution of tumor tissues, histopathological sections and the like; or for analysis and identification of cells, proteins and the like; or for affinity purification of cells or protein molecules including the ED-B protein domain. The present invention further provides use of the aforementioned kit in diagnosis of in vivo distribution of tumor tissues and histopathological sections; analysis and identification of cells and proteins; or affinity purification of cells or protein molecules including the ED-B protein domain. The present invention further provides use of the aforementioned kit in preparation of a kit used for diagnosis of in vivo distribution of tumor tissues and histopathological sections; analysis and identification of cells and proteins; or affinity purification of cells or protein molecules including the ED-B protein domain.

On the other hand, the present invention provides a polynucleotide molecule encoding the aforementioned antibody or antibody fragment.

In a specific implementation, the polynucleotide molecule includes a nucleotide sequence as shown in SEQ ID NO: 2, which encodes the amino acid sequence of antibody VH; and a nucleotide sequence as shown in SEQ ID NO: 4, which encodes the amino acid sequence of antibody VL.

Specifically, the present invention provides a monoclonal antibody against the human ED-B protein domain (abbreviated as B5), which is a fully humanized antibody, includes the VH and VL of human, and provides an linker fragment for connecting the VH and the VL. Particularly, the antibody B5 herein may be a single-chain antibody B5 (single-chain antibody fragment, scFv) which includes a VH, a VL and a linker, preferably constructed in the arrangement manner of antibody VH-linker-antibody VL. The VH has the amino acid sequence as shown in SEQ ID NO: 1; and the VL includes the amino acid sequence as shown in SEQ ID NO: 3. Preferably, the linker fragment includes the amino acid sequence as shown in SEQ ID NO: 5. In a specific implementation, the antibody B5 has the amino acid sequence as shown in SEQ ID NO: 15.

On the other hand, the present invention also provides a DNA molecule which encodes the aforementioned monoclonal antibody.

In an embodiment, the DNA molecule includes a nucleotide sequence as shown in SEQ ID NO: 2, which encodes the VH of the monoclonal antibody; a nucleotide sequence as shown in SEQ ID NO: 4, which encodes the VL of the monoclonal antibody; and optionally a nucleotide sequence as shown in SEQ ID NO: 6, which can be used for encoding the linker fragment for connecting the VH and the VL of the monoclonal antibody.

Furthermore, the present invention also provides a drug fusion protein used for therapy of tumors. This drug fusion protein is preferably in the form of B5-IL2, and the drug fusion protein includes the aforementioned monoclonal antibody B5 and a human interleukin 2 (abbreviated as IL2) with cytotoxicity. The monoclonal antibody B5 and the human IL2 protein are connected through a linker fragment. Preferably, the linker fragment includes the amino acid sequence as shown in SEQ ID NO: 7. Preferably the human IL2 is a recombinant human IL2 protein, which is a mature IL2 in which the signal peptide is removed. In a specific implementation, the fusion protein has the amino acid sequence as shown in SEQ ID NO: 16.

The term "monoclonal antibody" as described herein is also abbreviated as "McAb" and refers to a kind of specific antibody with high homogeneity, meaning that except few possibly existing naturally occurring mutants, the amino acid sequences and structures of respective antibodies are identical. The monoclonal antibody recognizes only one kind of epitope (antigenic determinant) and thus has high specificity. "Monoclonal" only represents that the source or composition of the antibodies is consistent, which is a description of the antibody characteristic, rather than representing a specific preparing method or technique.

The terms "antibody", "single-chain antibody", "antibody fragment" or "immunoglobulin" as used herein refer to a monomer or polymer composed of a VH and a VL of an antibody, wherein the heavy chain and the light chain may be connected through a covalent disulfide bond or a synthesized polypeptide. Each variable region may be connected with a constant region, or may be fused with other proteins.

The term "variable region" as described herein refers to that certain specific sequences of an antibody are varied significantly between different types of antibodies, wherein the variation of the variable region forms various antibodies for specifically recognizing specific antigens or epitopes. The variable region is concentrated at the N terminals of the heavy and light chains, which is a region varied significantly in the amino acid sequence and has a molecular weight of about 25,000 Daltons. The variable region includes three complementary determining regions (CDRs) (or also referred to as hypervariable region), and a relatively conservative region between the different CDR regions is called a framework region (FR). The CDR region is an antibody region used for recognizing and binding to an antigen, which directly determines the specificity of an antibody.

Herein, the constant region of antibody includes a heavy-chain constant region (CH) and a light-chain constant region (CL). As classified according to differences of amino acid sequences, the CH may be divided into five types respectively of IgA, IgD, IgE, IgG and IgM, wherein some of the types may be further subdivided; and the CL may be divided into two types respectively of κ and λ.

The "fusion protein" as described herein refers to a protein formed by serially connecting two or more natural proteins or artificially modified proteins through a gene engineering technique, wherein proproteins may be connected through artificially-designed polypeptide fragments or directly connected through peptide bonds. Generally, the fusion protein as described herein specifically refers to a fusion form of an antibody with other proteins, such as a bispecific antibody or multispecific antibody formed by the fusion of an antibody with other antibodies, or immunotoxin formed by the fusion of an antibody with cytotoxin. The adopted technical means are well known to those skilled in the art.

The term "polymer" as described herein refers to a polymer of protein monomers formed in a covalent form or non-covalent form. For example, the human antibody IgG is generally formed as a tetramer through covalent binding with disulfide bonds.

The term "radioactive isotope" as described herein refers to a radioactive nuclide, and commonly-used isotopes include Iodine-131, Iodine-125, phosphorus-32 and the like. A radioactive immune drug is prepared by labeling an antibody having high specificity and affinity against an antigen with a radioactive isotope, which can reach a targeted organ after being injected into the body and thus produces a biological effect of radiation.

The "pharmaceutical composition" as described herein refers to a new drug formed by cross-linking the antibody or antibody fragment with other chemical drugs or radioactive isotopes through chemical bonds; also refers to a fusion protein obtained by fusing the antibody or antibody fragment with other proteins (e.g., cytotoxin) and expressing the fusion form in a cell; also refers to a new targeted formulation formed by connecting the antibody or antibody fragment onto the surface of a nanoparticle; and also refers to a composition of the aforementioned antibody, antibody fragment, new drug, fusion protein or formulation with a pharmaceutically acceptable carrier.

The "kit" as described herein essentially consists of the antibody or antibody fusion protein described herein, or a new antibody composition formed through labeling the antibody or antibody fusion protein with a fluorescein, a radioactive isotope, a peroxidase, an alkaline phosphatase and the like. The kit optionally includes a buffer, an antibody not described herein, a substrate of enzymatic reaction (e.g., diaminobenzidine (DAB) and the like), and corresponding supporters such as an ELISA plate, magnetic beads and the like. The kit can be used for diagnosis of in vivo distribution of tumor tissues, histopathological sections and the like; or for analysis and identification of cells, proteins and the like; or for affinity purification of cells or protein molecules including the ED-B protein domain.

The "diagnosis" method as described herein refers to qualitative and quantitative detections of substances reflecting health conditions of the human body, such as body fluids, blood, tissues and the like, wherein the commonly-used experiment techniques include an immunohistochemical method, an immunocytochemical method, an enzyme linked immunosorbent assay and the like.

The "therapy" method as described herein refers to a process of administrating the antibody or antibody fragment, or a pharmaceutical combination formed therefrom into the human body through intravenous injection, local injection at the diseased region or the like, so as to generate the drug efficacy.

The present invention provides an antibody for specifically recognizing the ED-B protein, which includes the amino acid sequence of the heavy chain as shown in SEQ ID NO: 1 and the amino acid sequence of the light chain as shown in SEQ ID NO: 3. The antibody can produce its biological effect in various manners, but substantially the antibody fragment includes the sequence of the CDR3 region in the heavy chain or the sequence of the CDR3 region in the light chain.

The present invention also provides a DNA sequence of the antibody. In an embodiment, the adopted DNA includes the nucleotide sequence as shown in SEQ ID NO: 2, which can encodes the VH amino acid sequence of an antibody; and the nucleotide sequence as shown in SEQ ID NO: 4 which can encodes the VL amino acid sequence of an antibody.

Furthermore, the present invention also provides a method for preparing the aforementioned monoclonal antibody.

After the amino acid sequence or nucleotide sequence encoding the antibody of the present invention is obtained, those skilled in the art can prepare the fully humanized antibody of the present invention through conventional methods of the art. For example, the antibody can be prepared by using hybridoma techniques and gene engineering techniques well-known to those skilled in the art; or obtained by screening from hybridoma cell strains, or separating through a phage antibody library display technique.

The anti-ED-B monoclonal antibody of the present invention can be obtained by either cloning the single-chain antibody provided by the present invention into a protein expression vector, or cloning the nucleotide sequences of the heavy and light chains of the antibody respectively into different expression vectors or the same vector.

The protein expression vector as described herein includes but not limited to protein expression vectors of prokaryotic cells, yeast cells, insect cells, plant cells and mammal cells, wherein the vector includes acting elements necessary for expressing proteins in respective host cells, such as a promoter, a terminator, a resistance screening fragment and the like.

The DNA sequence encoding the monoclonal antibody of the present invention can be obtained through means well-known to those skilled in the art. For example, the DNA sequence is deduced according to the amino acid sequence, or obtained through extraction and reverse transcription of the mRNA, or obtained directly through artificial synthesis. Then these DNA sequences are inserted into expression vectors through technical means such as enzyme-cut and link up and the like, wherein the DNA sequence of the antibody is located in an appropriate reading frame and has necessary initiation codons and termination codons. The expression vector adopted in the present invention is a commercially-available expression vector well-known to those skilled in the art.

The constructed expression vector is transformed or transfected into a matched host cell, and then the antibody protein is expressed after cell culture under appropriate conditions.

The "host cell" includes a prokaryotic cell, a eukaryotic cell and the like. In the present invention, a eukaryotic host cell is preferred, and a mammal cell is more preferred. These cells can be obtained commercially or from cooperation organizations, wherein the cells include but not limited to Chinese hamster ovary (CHO) cells, human embryonic kidney cells (HEK293), African green monkey kidney cells (Vero cells), baby hamster kidney (BHK) cells, African green monkey kidney cells (COS), and various other immortalized cell lines. In the present invention, the CHO cell and the HEK293 cell are generally used as the host cell. These cell strains are well known in the art as being capable of providing modifications such as correct translation and protein folding, formation of disulfide bonds, glycosylation and the like to protein molecules, and are close to the natural state of a humanized protein. However, as well known by those skilled in the art, the aforementioned cell lines and subsets thereof all can express the antibody or fusion protein described in the present invention.

The methods for transformation and transfection of expression vectors into host cells include an electroporation technique, a liposome mediated method, a calcium phosphate precipitation method, a PEI mediated method and other methods, and those skilled in the art can select an appropriate transfection method based on different host cells and aims. For example, a vector carrying the nucleotide sequence of the antibody is transfected into a HEK293 cell through the PEI mediated method, and the lipidosome purchased from Invitrogen is transfected into a CHO cell to construct a cell strain which can express the antibody stably.

The purification method of the antibody in the present invention depends on the characteristics of the protein and the adopted protein tag. For example, when the antibody includes a fragment of the constant region of the antibody, a Protein A affinity chromatography method may be adopted; if the antibody includes six histidine tags, then a Ni-chelating affinity chromatography method may be used, or methods such as ion-exchange column chromatography, hydrophobic chromatography, molecular sieve chromatography, dialysis, gel electrophoresis and the like may be used. As such, the antibody of the present invention or a fusion protein including the antibody can be obtained by those skilled in the art only through conventional separation and purification methods.

The antibody of the present invention can be identified through various methods, such as the enzyme linked immunosorbent assay (ELISA) and the Western Blot assay, and the affinity detection of the antibody can be implemented with a BIAcore technique or Scatchard assay (Beatty, Beatty et al. 1987).

The antibody of the present invention can be fused with various proteins, or coupled with chemical drugs, nanoparticles and the like, so as to produce a targeting effect and form a targeted drug. The drug efficacy of the antibody or antibody fragment of the present invention and the corresponding targeted drugs can be proved from the cell level or the living organism level, and the proving of the drug efficacy can be achieved by those skilled in the art through conventional drug experiment methods.

Although the present invention is described in details above, it is apparent to those skilled in the art that various modifications and changes can be made to the present invention without departing from the design thought and protection scope of the present invention, and these modifications and changes within the scope of the present invention fall into the scope of the appended claims.

The present invention is further described in connection with embodiments hereafter. However, it should be understood that these listed embodiments are only used for illustration, rather than limiting the present invention.

DETAILED DESCRIPTION OF THE PREFERRED EMBODIMENT

Embodiment 1: Screening of Humanized Single-Chain Antibody Specific to the ED-B Domain in Human FN 1) Antigen Expression FN(B+), ED-B, FN(789) and FN(7B89) are cloned from the cDNA of the HEK293 cell, and then are each fused with six histidine tags at the carboxyl terminal. The proteins are expressed in $E.\ coli$, and the obtained recombinant proteins are purified through Ni-chelating affinity chromatography. For FN(7B89), the letter "B" represents that the expressed protein includes the ED-B domain; the "7, 8, 9" represents three domains adjacent to EDB in the FN; and FN(789) does not include the ED-B domain.

2) Construction of Antibody Library

A fully synthetic antibody library is designed for screening a single-chain antibody against the ED-B antigen. By using a most common human antibody molecule DP47 as the template of heavy chain and using DPK22 as the template of light chain, a template of the single-chain antibody library is formed by connecting the two templates sequentially through commonly-used $(G_4S)_3$ peptide bonds, wherein the CDR regions of the light and heavy chains are formed by addition according to experience. The DNA template of the antibody library is obtained through chemical synthesis. During the synthesis, Nco I and EcoR I restriction endonuclease cleavage sites are introduced to the 5'-terminal, and a Not I site is introduced to the 3'-terminal. The DNA is cloned onto a pCANTAB5E vector through the Nco I and Not I sites, so as to construct and generate a random antibody library and phage display, wherein the EcoR I site is used for subsequent molecular clone. For the random antibody library, the randomization of the CDR3 region is achieved through addition of restriction cleavage sites at two ends of the CDR3 regions of the light and heavy chains and the insertion of the restriction cleavage sites into a random fragment of the DNA (Marks, Hoogenboom et al. 1991, Hoogenboom and Winter 1992, Nissim, Hoogenboom et al. 1994, Pini, Viti et al. 1998, Silacci, Brack et al. 2005).

3) Screening

50 μl $E.\ coli$ TG1 bacteria solution of the antibody library is added into 50 ml fresh 2×YT culture media, subjected to shake culture at 37° C. until the OD600 value reaches 0.4-0.5, infected with a helper phage at 37° C. for 30 min, precipitated with PEG, then centrifuged at 10,000 g for 30 min, and resuspended in PBS for later use, to make the prepared phage-fused antibody library have a titer over $10^{12}$ CFU/ml.

The EDB antigen is enveloped in a 5 ml immune tube and blocked with milk, then 2 ml solution of the aforementioned phage antibody library in PBS is added. The culture is incubated at 37° C. for 2 hours, the liquid in the immune tube is poured out, and the culture is washed with 0.1% PBST for 20 times, and 4 ml log-phase TG1 bacteria is added and then incubated while standing at 37° C. for 1 hr. The bacteria solution is coated onto a SOB plate with ampicillin and glucose and cultured overnight, and then the $E.\ coli$ TG1 bacteria solution infected by the phage is collected to complete the first round of panning. The obtained TG1 bacteria solution is used for preparation of phage-fused antibody library again, so as to start the second round of panning.

Three rounds of panning are conducted in total by using the ED-B as the antigen, wherein the obtained E. coli TG1 is diluted at an appropriate ratio, and then coated onto an agarose plate to obtain monoclonal colonies used for respectively expressing soluble antibodies. An ELISA detection is conducted to select phage clones showing the brightest staining under the condition of the same enveloped antigen for further analysis.

4) Cloning of Antibody from Prokaryotic Vector to Eukaryotic Vector

The DNA fragment of the single-chain antibody obtained by panning is cleaved by EcoR I and Not I, then connected to a pCI-neo vector including the DNA sequence of the Fc fragment in the constant region of human IgG1 antibody, and the DNA sequence of the antibody is in the same open reading frame with the DNA sequence of IgG1Fc, so that the two DNA sequences can be expressed as a fusion protein, wherein IgG1Fc can be used for purifying the single-chain antibody and improving the stability of the antibody protein.

5) Protein Expression

After a large amount of obtained plasmids including the antibody fusion proteins are extracted, the DNA of the plasmids is infected into CHO-K 1 cells by using a liposome reagent Lipofectamine® 2000 from Invitrogen. The cells are selectively cultured in a selective culture medium including G418 for a continuous time of 4-8 weeks by means of the neo gene of the pCI-neo plasmid vector and then are clonally cultured through a limited dilution method, and the obtained monoclonal cells are further clonally cultured to obtain stably-expressed cell lines.

The obtained cell lines are habituated by using Hyclone SFM4CHO-Utility, and then expressed in suspension. As confirmed by ELISA and SDS-PAGE experiments, a target antibody protein is obtained with the yield of 100 mg/L.

6) Purification of Monoclonal Antibody

The antibody containing the 6×His tags is purified through Ni-chelating affinity chromatography from Qiagen, and the antibody containing Fc of the IgG1 constant region is purified through Protein A affinity chromatography from Genscript. The respective procedures are conducted according to the instructions.

Figure 1:
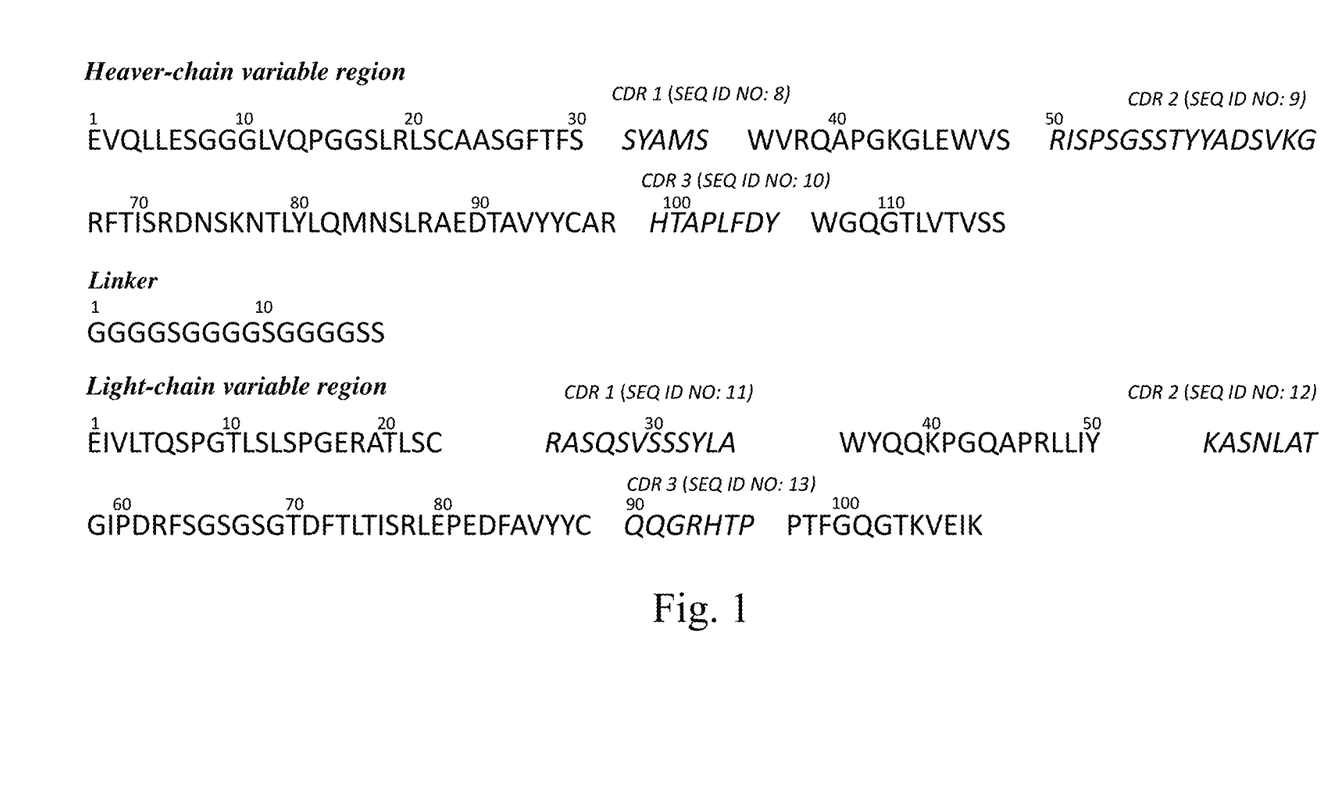
FIG. 1 illustrates the amino acid sequence of antibody B5.

Through this method, the antibody B5 of the present invention is obtained and the sequence thereof is shown in FIG. 1.

Embodiment 2: Specificity Detection of Antibody

1) Specificity Detection at Molecular Level

Figure 2:
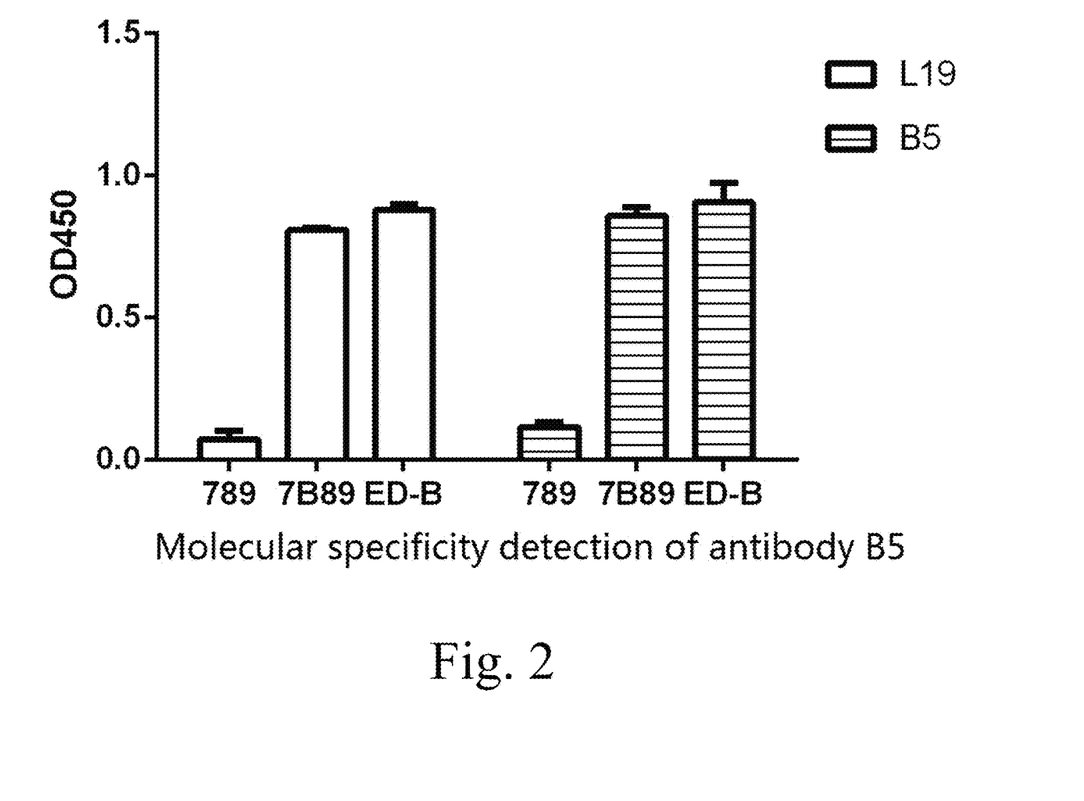
FIG. 2 illustrates an ELISA experiment adopted for confirming the ability of the antibody for specifically recognizing the ED-B domain of an antigen.

A truncated plasmid vector of fibronectin (FN) is constructed, which can respectively express proteins including the domain FN(789), proteins including the domain FN(7B89), and proteins including the independent ED-B domain, and has 6×His tags. The plasmid is expressed in E. coli and then purified through a Ni-chelating column. The aforementioned three proteins are used as antigens and are blocked with milk. Then an ELISA detection test is conducted by using the antibody B5 as a primary antibody and using the horseradish peroxidase-labeled rabbit-anti-human IgG antibody as the secondary antibody, with the test results being shown in FIG. 2. The results demonstrate that both the antibodies B5 and L19 show abilities of specifically recognizing the ED-B domain of the antigen. The staining value of the FN(789) domain is substantially consistent with that of a blank control in which the antigen is not enveloped, and the antibodies bind to both the independent ED-B domain and the FN(7B89) containing the ED-B domain.

2) Specificity Detection at Cellular Level

Figure 3:
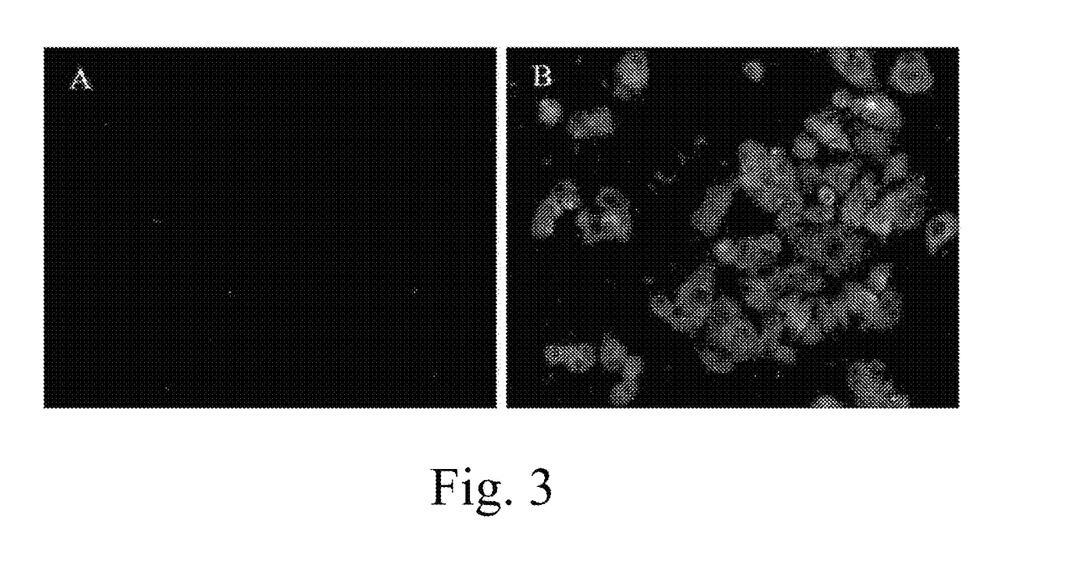
FIG. 3 illustrates a cellular immunofluorescence test used for confirming the ability of the antibody B5 for specifically recognizing an FN(B+) cell, wherein A is a negative control with no primary antibody and a secondary antibody being a FITC-labeled rabbit-anti-human IgG antibody; and B is the specific binding of the antibody B5 with the FN(B+) cell with a primary antibody being the antibody B5 and a secondary antibody being a FITC-labeled rabbit-anti-human IgG antibody.

Human rectal adenocarcinoma Caco-2 cells which highly express FN(B+) are added into and cultured in a glass bottom type laser confocal cell culture dish until the confluence reaches 30%, the culture medium is removed, and the culture is washed in PBS. Then the antibody B5 and a positive control are added, and PBS is used as a negative control. The culture is incubated at 37° C. for 2 hr, washed in PBS for three times, incubated for 1 hr with the FITC-labeled rabbit-anti-human IgG added as the secondary antibody, washed in PBS for three times, and then counterstained by adding DAPI. As observed in a laser confocal manner, the background of the negative control does not emit a green fluorescent light, while both the cell membranes of B5 and the positive control emit the green fluorescent light (as shown in FIG. 3), demonstrating that the antibody B5 can be specifically targeted to a Caco-2 cell expressing ED-B.

3) Specificity Research of Distribution in Animal Tissues

Construction of transplantation tumor mouse model: healthy Bal b/cnu nude mice are raised in a SPF barrier system until the tumor reaches 20 g per mouse, a transplantation tumor tissue mass from a human pharyngeal squamous carcinoma cell FaDu with the volume of about 1 $mm^3$ is subcutaneously implanted on the back of each mouse, and then the mice are raised continually.

Fluorescence labeling of antibody drug: the antibody B5 is labeled with the Cy5.5 NHS ester fluorescent dye, and the labeling ratio of the antibody protein to the fluorescent dye molecule is 1:1.

Administration method: when the tumor is grown to have a diameter of about 5 mm, the antibody labeled with the Cy5.5 is introduced according to the standard of 5 mg per kg weight of the tumor. The in vivo distribution condition of the antibody is observed by using a small animal in vivo imaging system from Xenogen, and the observation is conducted once per day after administration.

Figure 4:
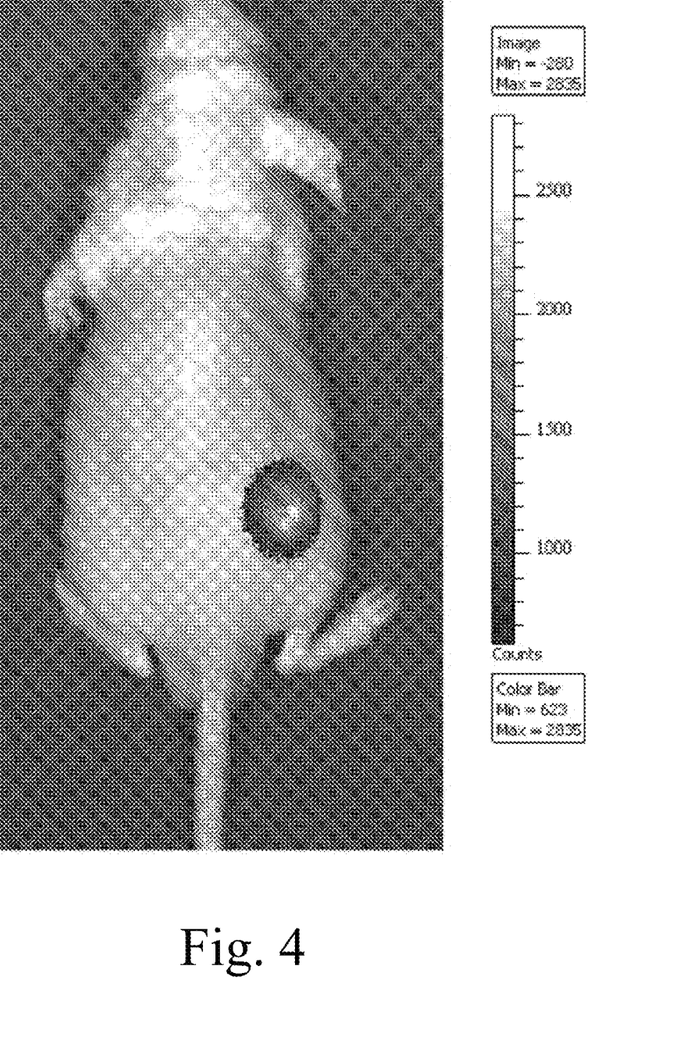
FIG. 4 illustrates the distribution condition of the Cy5.5 NHS ester-labeled antibody B5 at the time 24 hours after the administration thereof through tail intravenous injection to a Balb/c nu nude mouse.

The experiment results are shown in FIG. 4. The antibody drug is significantly enriched in tumor tissues 24 hours after the administration, the distribution of the Cy5.5 fluorescent dye is not detected in other tissues, and the fluorescent light can be maintained in the tumor tissues after administration for over 7 days.

Embodiment 3: Determination of Antibody Affinity

1) Determination of Absolute Affinity of Antibody Against ED-B Antigen through ELISA Method The Scatchard assay method (Beatty, Beatty et al. 1987) is used for the affinity determination. 0.1 µg/µl ED-B antigen is diluted according to four concentration gradients of 1:1, 1:2, 1:4 and 1:8, enveloped in the ELISA plate, stored overnight at 4° C., and then blocked with 4% skimmed milk. The single-chain antibody diluted according to the concentration gradient of 1:3 is added with the original concentration of the antibody being 10 µg/ml. The antibody reacts under a room temperature for 1 hr, then reacts for 1 hr under the addition of a horseradish peroxidase-labeled rabbit-anti-human IgG antibody, and is stained by adding tetramethyl benzidine (TMB). When an appropriate color depth is reached, the staining is terminated by using 2M $H_2SO_4$, and the OD450 optical absorption value is determined.

As calculated, the result shows that the equilibrium dissociation constant KD of the antibody B5 is 1.8 nM, while the equilibrium dissociation constant KD of the antibody L19 is 6.0 nM, so that the affinity of the antibody B5 is higher than that of the antibody L19.

2) Determination of Absolute Affinity of Antibody Against ED-B Antigen through Biocore3000

A monolayer carboxyl chip (coupled with the amino group of a protein) is used to envelope the antigen, wherein the antigen EDB (with the concentration of 10 μg/ml) is diluted into a fixed phase by using an acetic acid buffer solution with the pH of 4. The chip is blocked by using a 1M ethanolamine-HCl buffer solution with the pH of 8.5.

An appropriate concentration gradient should be selected for determination of kinetic constants. The antibodies of the aforementioned four concentration gradients are further diluted according to a gradient of 1:2, such that totally eight concentrations are used as flowing phases, with each concentration being sampled in parallel for three times. The dynamic binding and distribution states of the fixed and flowing phases are detected through the BIAcore3000.

As detected, the antibody B5 can specifically bind onto the ED-B antigen, and the binding between the B5 and the EDB on the surface of the chip is hardly ever dissociated, i.e. the dissertation degree exceeds the detection limit of instrument, which indicates that the antibody B5 can stably bind to the ED-B antigen. The equilibrium dissociation constant of the antibody L19 is 0.4 nM, as detected via the BIAcore3000.

Embodiment 4: Stability Test of Antibody in Blood Plasma

The B5 is diluted respectively to 1 ng/μl and 0.1 ng/μl with the blood plasma of Bal b/c mice, transferred into EP tubes, each tube including 100 μl of the solution. The tubes are incubated in a water bath of 37° C. respectively for 0, 4, 8 and 24 hr. The tubes are withdrawn from the water bath at the same time to conduct an ELISA detection thereof.

The procedure of ELISA detection is as follows: the FN(7B89) fusion protein is enveloped in the ELISA plate at 4° C. overnight; the protein reacts under room temperature for 2 hr, with B5-IgG1Fc being used as the primary antibody and the horseradish peroxidase-labeled rabbit-anti-human IgG being used as the secondary antibody; the protein is stained under room temperature by using the tetramethyl benzidine (TMB) as a substrate, and then detection is conducted at a wavelength of 450 nm via a microplate reader. The result shows that after the antibodies of two different concentrations are incubated in the mice's blood plasma for different time periods, the immune activity changes of the antibodies are statistically meaningless.

Figure 5:
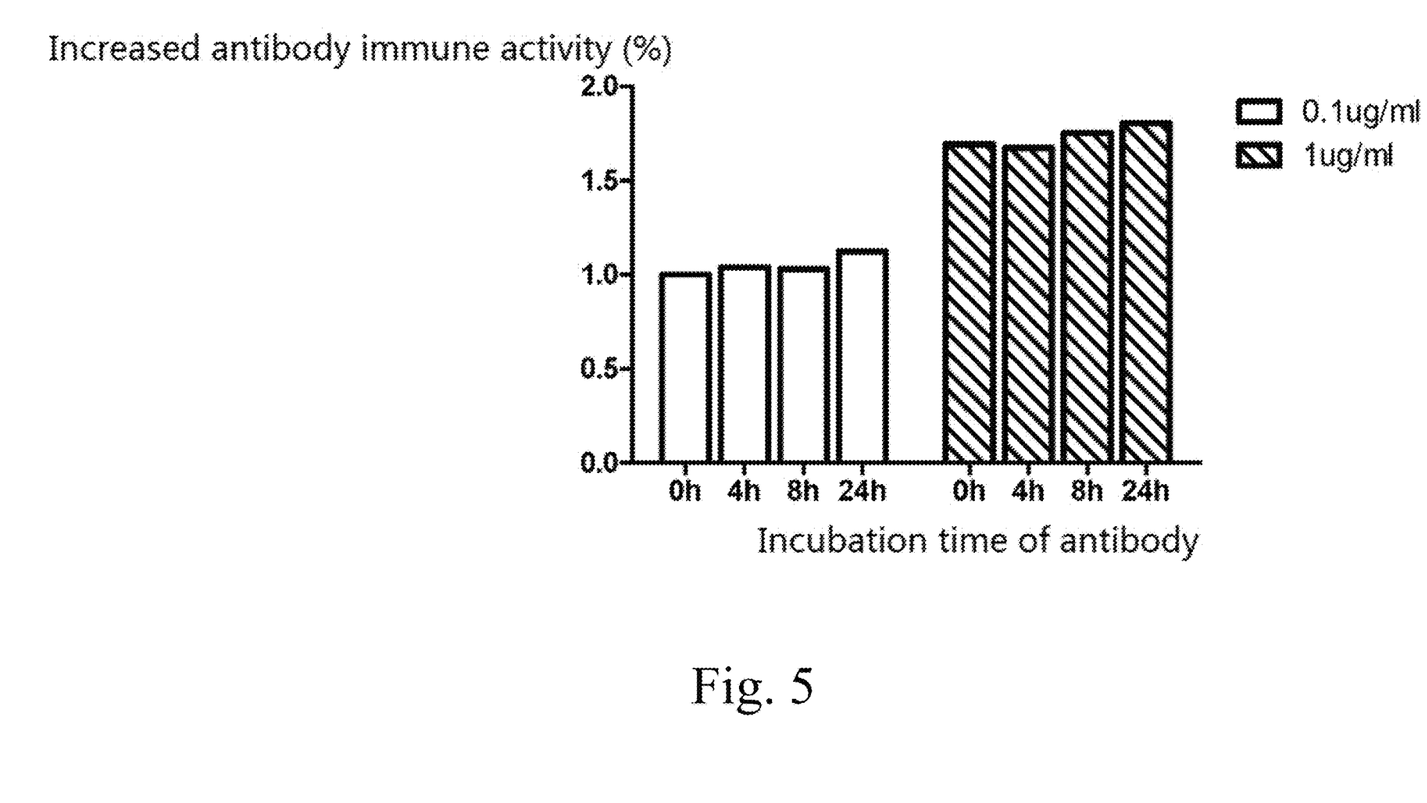
FIG. 5 illustrates a thermal stability test of the antibody B5.

By using 0.1 μg/ml B5 antibody incubated in the blood plasma for 0 hr as a standard, changes of the activities of antibodies with different concentrations and under different incubation conditions relative to the standard activity are observed. Therefore, it can be seen that after the antibody is diluted to 1 μg/ml or 0.1 μg/ml with the blood plasma and incubated at 37° C. for 4, 8 and 24 hr, the activity of the antibody is not reduced obviously as compared to the standard 0 hr (as shown in FIG. 5), demonstrating that the antibody B5 can keep stable in the blood plasma of Bal b/c mice.

Embodiment 5: Research of Physiological Activities of Monoclonal Antibody

Construction of transplantation tumor mouse model: healthy Bal b/c mice are raised until the tumor reaches 20 g per mouse, and mice's embryonic cancer cells F9 are subcutaneously injected under the foreleg armpit with the amount of $3 \times 10^6$ per mouse, so as to construct a model.

Administration method: when the solid tumor can be identified clearly, an antibody drug B5-IL2 (the fusion protein has the amino acid sequence as shown in SEQ ID NO: 16) of 30 μg is administrated to each mouse through tail intravenous injection, and the drug administration is repeated once three days later. The positive control is B5m-IL2, wherein B5m is a mutant antibody which cannot bind specifically to the ED-B, which is formed by the lactamine mutation in the CDR3 region of the B5 heavy chain. The mutation method is the process that the amino acid HTAPLFDY in the CDR3 region of B5 heavy chain is mutated into lactamine AAAAAAAA (SEQ ID NO: 14) while other sequences are kept unchanged, and the resultant mutant of antibody B5 is known as B5m.

Determination of tumor growth rate: the size of the tumor is measured every day until the mice's tumor is increased to 1000 mm³ or after 14 days, then the mice are sacrificed. Calculation method of tumor volume: the maximum diameter (Length) and the minimum diameter (Width) of the tumor are measured by using a vernier caliper, wherein the tumor volume=width²×length×0.5.

The experiment results are shown in table 1 below, wherein no significant difference in tumor size exists between the positive control group and the negative control group, the mean tumor volume of the experiment group is about three times more than that of the negative control group, and the differences in tumor volume between the experiment group and the two control groups have statistical meaning (p<0.05).

TABLE 1

Therapeutic Effect of B5-IL2 through tail intravenous injection to a Balb/c mouse ($\bar{x} \pm s$, n = 6, *p < 0.05)

| Group | Tumor Volume (mm³) | Reduction Folds of Tumor Volume Compared with the Control Group |
|---|---|---|
| Negative Control Group | 0.53 ± 0.13 | — |
| Positive Control Group | 0.51 ± 0.13 | — |
| Experiment Group | 0.17 ± 0.07* | 3 folds |

What is claimed is:

1. An antibody or antibody fragment for specifically recognizing and binding to an ED-B domain of human fibronectin (FN), comprising a VH having an amino acid sequence as shown in SEQ ID NO: 1 and a VL having an amino acid sequence as shown in SEQ TD NO: 3.

2. The antibody or antibody fragment, as recited in claim 1, wherein the antibody or antibody fragment is a monoclonal antibody with an equilibrium binding/dissociation constant (KD) of $1\times10^{-8}$ M or less, $1\times10^{-9}$ M or less, or $1\times10^{-10}$ M or less.

3. The antibody or antibody fragment, as recited in claim 1, wherein the antibody or antibody fragment is a mammal-derived antibody sequence.

4. The antibody or antibody fragment, as recited in claim 1, wherein the antibody or antibody fragment directly binds to the ED-B protein domain.

5. The antibody or antibody fragment, as recited in claim 4, wherein the ED-B protein domain is an independent recombinant ED-B protein, or a recombinant protein formed through fusion of the ED-B protein with other proteins, or a natural fibronectin comprising the ED-B domain.

6. The antibody or antibody fragment, as recited in claim 4, wherein the ED-B protein domain is derived from humans, mice, rats, or chickens.

7. The antibody or antibody fragment, as recited in claim 1, wherein the antibody is a human immunoglobulin IgG.

8. A pharmaceutical composition for diagnosing or treating tumor disease comprising the antibody or antibody fragment as recited in claim 1.

9. The pharmaceutical composition, as recited in claim 8, further comprising a fusion protein, a radioactive isotope, a chemical drug and a nanoparticle.

10. The pharmaceutical composition, as recited in claim 9, wherein the cancer disease is a cancer in which the FN(B+) comprising the ED-B domain is expressed.

11. The pharmaceutical composition, as recited in claim 10, wherein the cancer disease is nasopharyngeal cancer, larynx cancer, oesophagus cancer, cardiac cancer, gastric cancer, colorectal cancer, lung cancer, liver cancer, pancreatic cancer, melanoma, fibrosarcoma or breast cancer.

* * * * *